United States Patent
Pi et al.

(10) Patent No.: US 10,723,724 B2
(45) Date of Patent: Jul. 28, 2020

(54) COMPOUNDS FOR TREATING DEGENERATIVE DISEASES OF CENTRAL NERVOUS SYSTEM OR BRAIN TUMOR, AND USES THEREOF

(71) Applicant: SUN YAT-SEN UNIVERSITY, Guangdong (CN)

(72) Inventors: Rongbiao Pi, Guangdong (CN); Yalin Tu, Guangdong (CN); Qiuhe Chen, Guangdong (CN); Xiaohong Yang, Guangdong (CN); Shengnan Wang, Guangdong (CN); Jingkao Chen, Guangdong (CN); Shijun Wen, Guangdong (CN)

(73) Assignee: SUN YAT-SEN UNIVERSITY, Guangzhou, Guangdong (CN)

( * ) Notice: Subject to any disclaimer, the term of this patent is extended or adjusted under 35 U.S.C. 154(b) by 0 days.

(21) Appl. No.: 16/325,669

(22) PCT Filed: Dec. 9, 2016

(86) PCT No.: PCT/CN2016/109199
§ 371 (c)(1),
(2) Date: Feb. 14, 2019

(87) PCT Pub. No.: WO2018/032666
PCT Pub. Date: Feb. 22, 2018

(65) Prior Publication Data
US 2019/0202817 A1 Jul. 4, 2019

(30) Foreign Application Priority Data
Aug. 15, 2016 (CN) .......................... 2016 1 0667749

(51) Int. Cl.
| | | |
|---|---|---|
| *C07D 409/12* | (2006.01) | |
| *A61K 31/4545* | (2006.01) | |
| *C07D 409/14* | (2006.01) | |
| *A61K 31/4436* | (2006.01) | |
| *A61P 25/28* | (2006.01) | |
| *A61P 35/00* | (2006.01) | |
| *A61K 31/4725* | (2006.01) | |

(52) U.S. Cl.
CPC ........ *C07D 409/12* (2013.01); *A61K 31/4436* (2013.01); *A61K 31/4545* (2013.01); *A61K 31/4725* (2013.01); *A61P 25/28* (2018.01); *A61P 35/00* (2018.01); *C07D 409/14* (2013.01)

(58) Field of Classification Search
CPC .... C07D 409/12; A61K 31/4436; A61P 25/28
USPC .......................................................... 549/40
See application file for complete search history.

(56) References Cited

U.S. PATENT DOCUMENTS 5,888,694 A * 3/1999 Yamada .................. G03C 1/06
430/264
6,605,637 B1 * 8/2003 Harnett ................ C07C 323/60
514/440

FOREIGN PATENT DOCUMENTS

| CN | 103649077 A | 3/2014 |
| CN | 104220421 A | 12/2014 |
| CN | 105949180 A | 9/2016 |

OTHER PUBLICATIONS

How to treat Alzheimer's, NIA, National Institute on Aging (Year: 2018).*
Tu, Ya-lin et al.; "Discovery of lipoic acid-4 phenyl-1H-pyrazole hybrids as novel bifunctional ROCK inhibitors with antioxidant activity"; The Royal Society of Chemistry—Advances; Jun. 13, 2016; vol. 6; pp. 58516-58520.

* cited by examiner

*Primary Examiner* — Rita J Desai
(74) *Attorney, Agent, or Firm* — Muncy, Geissler, Olds & Lowe, P.C.

(57) ABSTRACT

The present invention relates to a compound for treating a degenerative disease of central nervous system or a brain tumor, a composition and a use thereof, wherein the compound has the structure of Formula I.

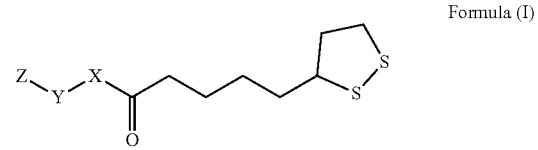

Formula (I)

These compounds can be used as SGK1 and JNK dual inhibitors with antioxidant effect, which can be formulated into suitable formulations for treating a degenerative disease of central nervous system or a brain tumor.

2 Claims, 1 Drawing Sheet

COMPOUNDS FOR TREATING DEGENERATIVE DISEASES OF CENTRAL NERVOUS SYSTEM OR BRAIN TUMOR, AND USES THEREOF

FIELD OF THE INVENTION

The present invention relates to the field of medicine, and specifically to a compound for treating degenerative diseases of central nervous system or brain tumor, composition and use thereof. The present invention also relates to a series of methods for manufacturing a SGK1 and JNK dual inhibitor having antioxidant activity and use thereof, which can be formulated into a suitable formulation for treating degenerative diseases of central nervous system or brain tumor.

BACKGROUND OF THE INVENTION

Serum and glucocorticoid-inducible kinase1 (SGK1) is a serine-threonine kinase which was identified by Webster et al. through a differential expression screen of the glucocorticoid-induced rat mammary tumor cell. When the cell was stimulated by glucocorticoid or serum, the transcription level of SGK1 was rapidly elevated within 30 min. It is thus referred to as serum and glucocorticoid-inducible kinase. SKG1 shares high homology with second messengers such as protein kinase B (PKB/Akt). In addition to the phosphorylation and dephosphorylation regulation mechanism as similar to most protein kinases, SGK1 is also regulated in rapid transcript phase. According to reports in the literature, SGK1 is regulated by a plurality of hormones and growth factors, such as glucocorticoid, serum, mineralocorticoid, polypeptide hormone CRH and the like, which can rapidly induce the expression of SGK1. More and more studies indicate that SGK1 is a functional intersection between a plurality of cellular signal transduction pathways and cellular phosphorylation cascade, which involves with a variety of physiological functions such as signal transduction of regulation of ion channel, cell survival, differentiation, proliferation and apoptosis, and the like. Recent work has found that it is closely related to cerebral degenerative disease such as cerebral ischemia, epilepsy, Alzheimer's disease (AD), Parkinson's disease (PD), brain tumor, and the like. It plays an important role in central nervous system development, neuronal degeneration and apoptosis, and the occurrence and development of brain tumors. Abnormal increases in the expression and activity of SGK1 are involved in the development and progression of various diseases, and inhibitors of SGK1 are considered to be potential drugs for the treatment of these diseases.

The c-Jun N-terminal kinase (JNK) family is one of the members of the mitogen-activated protein kinase (MAPK) superfamily discovered in 1990, and is evolutionarily conserved serine/threonine protein kinase. The JNK signaling pathway is activated by various factors such as cytokines, growth factors, stress and the like, and plays a predominant role in cell regulation such as cell proliferation and differentiation, cell apoptosis and stress response. Dysfunction of JNK signaling pathway may result in various diseases such as ischemia-reperfusion injury, chronic inflammation, neurodegeneration, diabetes, tumors and the like. Recent studies have found that the over-activated JNK signaling pathway is closely related to Alzheimer's disease and Parkinson's disease, while knockout of JNK or JNK inhibitors can ameliorate the symptoms of AD and PD disease models. Certain studies have discovered that overexpression of JNK was shown in patients suffering from glioma, and the expression level of JUK is highly related to the grade malignancy of glioma and prognosis of the patients suffering from glioma. In addition, JNK inhibitors have been found to suppress the self-renewal capacity of glioma stem cells and to promote the differentiation of glioma stem cells into glia-like or neuron-like cells which are not tumorigenic. Therefore, JNK inhibitors are considered to be potential drugs for diseases such as neurodegenerative disease and brain tumor.

Lipoic acid (LA) is one of the most powerful natural antioxidants and known as the universal antioxidant. It is a cofactor for pyruvate dehydrogenase, and also a metabolism antioxidant. In the organism, LA can be transformed into the reduced dihydrolipoic acid (DHLA). Antioxidant effect can be obtained by scavenging free radicals and reactive oxygen, chelating metal ion and interacting with other antioxidants. Lipoic acid has the characteristics of low molecular weight and amphiphilicity, which make it easy to penetrate the blood-brain barrier, such that it can exert anti-oxidation effect in the central nervous system. Therefore, it is considered to be an effective way to treat neurodegenerative diseases. However, lipoic acid is not stable enough in the body, and is simply single targeted. LA with single antioxidation effect is difficult to be used alone in CNS diseases with complicated pathogenesis. Clinically, it is mainly used in combination with other drugs, or used as a pharmacophore for multi-target drug development.

As describe above, both SGK1 and JNK are highly expressed in diseases such as degenerative diseases of central nervous system or brain tumor. The suppression of SGK1 or JNK would improve the progress of diseases (such as degenerative diseases of central nervous system, brain tumor and the like) to some extent. The antioxidants also play a positive role in the treatment of the degenerative diseases of central nervous system. Complex diseases (such as degenerative diseases of central nervous system, tumors and the like) with a complicated pathogenesis and pathogenic factors interacted with each other is difficult to be treated or improved by a single drug. With the development of system biology and network pharmacology, multi-target drugs that can simultaneously act on multiple targets associated with pathogenesis is increasingly expected to be applied to the treatment of such diseases. On this basis, the present invention aims to develop a small molecule compound having dual inhibition of SGK1 and JNK and an anti-oxidation effect, thereby obtaining additive or synergistic effects in the treatment of diseases such as degenerative diseases of central nervous system and brain tumor. At the same time it can reduce inconvenience of drug combination, drug-drug interaction and other adverse factors.

SUMMARY OF THE INVENTION

On the basis of above studies and multi-target drugs development strategy, we synthesized and screened a series of small molecule compounds with SGK1 and JNK dual inhibition activity.

The present invention is related to a compound of Formula I, or tautomer, pharmaceutically acceptable salt, pro-drug or solvate thereof, wherein

X is:

or ;

Y is:

or ;

Z is:

or .

Unless otherwise stated, the compounds of the invention are also meant to include compounds which differ only in the presence of one or more isotopically enriched atoms. For example, compounds having the replacement of a hydrogen by a deuterium or tritium, or the replacement of a carbon by a $^{13}C$- or $^{14}C$-enriched carbon or the replacement of a nitrogen by $^{15}N$-enriched nitrogen are within the scope of this invention.

The term "pharmaceutically acceptable salts, derivatives, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art. For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Preferred derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The reaction products may, if desired, be purified by conventional methods, such as crystallization or chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in a pharmaceutical composition. In the case of salts and solvates the additional ionic and solvent moieties must also be non-toxic. The compounds of the invention may present different polymorphic forms, it is intended that the invention encompasses all such forms.

The typical compounds represented by the above-mentioned formula (I) of the present invention, a salt thereof, a solvate or a prodrug of them exhibit a favorable permeation rate of blood-brain barrier. Therefore, another aspect of this invention relates to a method of treating, improving or preventing a neurodegenerative disease of central nervous system which method comprises administering to a patient in need of such a treatment a therapeutically effective amount of a compound of formula (I) or a pharmaceutical composition thereof.

The present invention further provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

The compounds and compositions of this invention may be used with other drugs to provide a combination therapy. The other drugs may form part of the same composition, or be provided as a separate composition for administration at the same time or at different time.

DETAILED DESCRIPTION OF THE INVENTION

The following examples are provided to further illustrate the present invention by way of example, they should not be taken as a limitation on the scope of the invention. Unless otherwise stated, the regents and methods involved in the following examples are reagents and methods commonly used in the art, wherein DCM, TFA, EDCI and DMAP as used herein refer, respectively, to dichloromethane, trifluoroacetic acid, 1-(3-dimethylaminopropyl)-3-ethylcarbodiimide hydrochloride and 4-dimethylaminopyridine.

Example 1

Preparation of 5-(1, 2-dithiolan-3-yl)-N-(2-(isoquinoline-5-sulfonamido) ethyl) pentanamide (PT019)

Synthetic Scheme:

PT019

According to the above scheme of PT019, isoquinoline-5-sulfonic acid was placed in a round-bottom flask, then thionyl chloride (6 mL) and DMF (one drop) was added. The reaction is refluxed for 3 h. The thionyl chloride was removed by a rotary evaporator. DCM was added to the residual solid, and the reaction was filtrated. The solid was washed thrice with DCM, then dried by a vacuum drying oven to give an intermediate 2 as a white solid (1 g, yield 91.9%).

To a solution of ethylenediamine (381.30 μL, 5.71 mmol) in DCM (6 mL), the intermediate 2 (130.00 mg, 571.01 μmol) was slowly added in an ice bath. The ice bath was removed, then the reaction was at the room temperature for 3 h. Following the completion of the reaction, the residual ethylenediamine was washed with water. The solvent was removed from the organic phase by a rotary evaporator. The residue was recrystallized in diethyl ether to give an intermediate 3 as a pale brown solid (91.8 mg, yield 60%). $^1$H NMR (400 MHz, DMSO) δ 9.48 (s, 1H), 8.70 (d, J=6.1 Hz, 1H), 8.47-8.40 (m, 2H), 8.34 (dd, J=7.4, 1.1 Hz, 1H), 7.87-7.80 (m, 1H), 2.77 (t, J=6.5 Hz, 2H), 2.46 (t, J=6.5 Hz, 2H).

The intermediate 3 (100 mg, 397.92 μmol), lipoic acid (98.52 mg, 477.51 μmol) and DMAP (4.86 mg, 39.79 μmol) were dissolved in the DCM (6 mL), then Et$_3$N (165.48 μL, 1.19 mmol) and EDCI (114.42 mg, 596.88 μmol) were added to the solution. The reaction was stirred overnight at room temperature, diluted with DCM (30 mL) later, and stopped by water (10 mL). After isolation, the aqueous phase was extracted with DCM (15 mL×3). The combined organic phase was washed with a saturated brine solution (10 mL×1). It was dried over Na$_2$SO$_4$, then rotary evaporated to remove the solvent. The residue was purified by silica gel column chromatography to afford a yellow sticky oil PT019 (168 mg, yield 96%). $^1$H NMR (400 MHz, CDCl$_3$) δ 9.36 (s, 1H), 8.70 (d, J=6.1 Hz, 1H), 8.48-8.35 (m, 2H), 8.22 (d, J=8.2 Hz, 1H), 7.77-7.65 (m, 1H), 5.94 (dd, J=10.0, 4.8 Hz, 2H), 3.56 (dt, J=14.8, 6.3 Hz, 1H), 3.34 (dd, J=11.1, 5.8 Hz, 2H), 3.14 (dddd, J=22.8, 16.0, 8.9, 5.5 Hz, 4H), 2.46 (dt, J=12.3, 6.5 Hz, 1H), 2.16-2.03 (m, 2H), 1.91 (td, J=13.7, 6.9 Hz, 1H), 1.61-1.53 (m, 2H), 1.48-1.32 (m, 2H). $^{13}$C NMR (101 MHz, CDCl$_3$) δ 174.29, 153.28, 145.02, 134.25, 133.69, 133.23, 131.17, 129.08, 126.08, 117.36, 56.46, 43.28, 40.28, 39.38, 38.49, 36.14, 34.50, 28.78, 25.21. Purity: 97% (HPLC).

Example 2

Preparation of 5-(1, 2-dithiolan-3-yl)-N-(3-(isoquinoline-5-sulfonamido) propyl) pentanamide (PT046)

The Synthetic Scheme:

According to the above synthetic scheme of PT046, to a solution of 1,3-propane diamine (1.89 mL, 22.72 mmol) in DCM (6 mL), the intermediate 3 obtained in the example 1(600.00 mg, 2.27 mmol) was added slowly in an ice bath. The ice bath was removed, then the reaction was at the room temperature for 3 h. Following the completion of the reaction, the residual ethylenediamine was washed with water. The solvent was removed from the organic phase by a rotary evaporator. The residue was recrystallized in the diethyl ether to give an intermediate 4 as a pale brown solid (300 mg, yield 43.8%).

The intermediate 4 (77.16 mg, 290.80 μmol), lipoic acid (50.00 mg, 242.34 μmol) and DMAP (2.96 mg, 24.23 μmol) were dissolved in the DCM (6 mL), then $Et_3N$ (6 mL) and EDCI (69.68 mg, 363.50 μmol) were added to the solution. The reaction was stirred overnight at room temperature, diluted with DCM (30 mL) later, and stopped by water (10 mL). After isolation, the aqueous phase was extracted with DCM (15 mL×3). The combined organic phase was washed with a saturated brine solution (10 mL×1). It was dried over $Na_2SO_4$, then rotary evaporated to remove the solvent. The residue was purified by silica gel column chromatography to afford a yellow sticky oil PT046 (19.2 mg, yield 17.5%). $^1H$ NMR (400 MHz, CDCl3) δ 9.34 (s, 1H), 8.70 (d, J=6.1 Hz, 1H), 8.47 (d, J=6.1 Hz, 1H), 8.41 (dd, J=7.3, 1.1 Hz, 1H), 8.19 (d, J=8.2 Hz, 1H), 7.73-7.63 (m, 1H), 6.49 (t, J=6.5 Hz, 1H), 5.82 (t, J=5.9 Hz, 1H), 3.52-3.43 (m, 1H), 3.28 (dd, J=12.2, 6.3 Hz, 2H), 3.20-3.04 (m, 2H), 2.92 (dd, J=12.2, 6.4 Hz, 2H), 2.48-2.38 (m, 1H), 2.11 (t, J=7.3 Hz, 2H), 1.94-1.77 (m, 4H), 1.70-1.62 (m, 1H), 1.55-1.46 (m, 2H), 1.40-1.28 (m, 2H). $^{13}C$ NMR (101 MHz, CDCl3) δ 174.10, 153.16, 145.16, 135.06, 133.35, 132.85, 131.26, 129.05, 125.94, 117.55, 56.42, 40.27, 39.73, 38.48, 36.26, 35.80, 34.48, 30.10, 28.76, 25.25. Purity: 96% (HPLC).

Example 3

Preparation of 5-(1, 2-dithiolan-3-yl)-N-(4-(isoquinolin-5-ylamino) cyclohexyl) pentanamide (PT109)

The Synthetic Scheme:

According to the above synthetic scheme of PT109, the compound 5 (442.31 mg, 2.07 mmol), isoquinolin-5-amine (230.00 mg, 1.60 mmol) and anhydrous $Na_2SO_4$ (1.13 g, 7.98 mmol) were dissolved in glacial acetic acid (10 mL). Sodium cyanoborohydride (200.50 mg, 3.19 mmol) was added in the ice bath. The ice bath was removed, and the reaction was stirred overnight at room temperature. Following the completion of the reaction, the glacial acetic acid was removed from the organic phase by a rotary evaporator. A saturated $NaHCO_3$ solution was added to the residue. The aqueous phase was extracted with DCM. The combined organic phase was washed with a saturated brine solution (10 mL×1). It was dried over $Na_2SO_4$, then rotary evaporated to remove the solvent. The residue was purified by silica gel column chromatography to give compound 6 as a yellow solid (372 mg, yield 68.3%). $^1H$ NMR (400 MHz, CDCl3) δ 9.15 (s, 1H), 8.46 (s, 1H), 7.53 (s, 1H), 7.49-7.39 (m, 1H), 7.30 (s, 1H), 6.77 (s, 1H), 4.71-4.12 (m, 2H), 3.55 (m, 3H), 2.27 (d, J=12.0 Hz, 1H), 2.14 (d, J=12.6 Hz, 1H), 2.06-1.88 (m, 2H), 1.82 (m, 2H), 1.46 (s, 9H), 1.34 (m, 3H).

Compound 6 (45.51 mg, 133.28 μmol) was dissolved in DCM (1 mL), then TFA (1 mL) was added. The reaction was stirred at the room temperature for 3 h. Following the completion of the reaction, TFA was removed by a rotary evaporator. Lipoic acid (25.00 mg, 121.17 μmol), HOBt (18.01 mg, 133.28 μmol) and EDCI (34.84 mg, 181.75 μmol) were added to the residue. Then triethylamine (50.39 μL, 363.50 μmol) in the anhydrous DCM was added. The reaction was stirred overnight at room temperature. Following the completion of the reaction, the reaction was quenched with water (10 mL). The aqueous phase was extracted with DCM. The combined organic phase was washed with a saturated brine solution (10 mL×1). It was dried over $Na_2SO_4$, then rotary evaporated to remove the solvent. The residue was purified by silica gel column chromatography to afford a yellow oil PT109 (39.3 mg, yield 75.5%). m.p. 131.4° C. $^1$H NMR (400 MHz, CDCl3) δ 9.14 (s, 1H), 8.44 (d, J=5.9 Hz, 1H), 7.54 (d, J=5.9 Hz, 1H), 7.46 (t, J=7.9 Hz, 1H), 7.30 (d, J=8.1 Hz, 1H), 6.77 (d, J=7.7 Hz, 1H), 6.00 (d, J=7.4 Hz, 1H), 4.01 (d, J=7.4 Hz, 1H), 3.70 (s, 1H), 3.62-3.48 (m, 1H), 3.24-3.02 (m, 2H), 2.43 (tt, J=20.8, 10.4 Hz, 1H), 2.20 (t, J=7.3 Hz, 2H), 2.00-1.78 (m, 7H), 1.70 (m, 7H), 1.56-1.37 (m, 3H). $^{13}$C NMR (100 MHz, CDCl$_3$) δ 173.25, 171.31, 153.00, 143.11, 131.58, 130.07, 129.03, 127.30, 125.40, 114.24, 56.46, 45.00, 43.66, 41.11, 40.28, 38.53, 34.73, 33.13, 29.19, 28.93, 25.06. Purity: 100% (HPLC).

Example 4

Preparation of 5-(1, 2-dithiolan-3-yl)-1-(3-(isoquinolin-5-ylamino) piperidin-1-yl) pentan-1-one (PT128)

The Synthetic Scheme:

According to the above synthetic scheme of PT128, compound 7 (497.52 mg, 2.50 mmol) and isoquinolin-5-amine (300.00 mg, 2.08 mmol) was dissolved in the isopropyl titanate (5 mL). The reaction was stirred at room temperature for 30 min., then absolute ethyl alcohol (5 mL) was added to dilute. Sodium cyanoborohydride (261.53 mg, 4.16 mmol) was added in an ice bath, and the reaction was stirred at room temperature for 3 h. The solid was removed by celite filtration and the reaction was quenched with a saturated $NaHCO_3$ solution. The aqueous phase was extracted with ethyl acetate. The combined organic phase was washed with a saturated brine solution (10 mL×1). It was dried over $Na_2SO_4$, then rotary evaporated to remove the solvent. The residue was purified by silica gel column chromatography to give Compound 8 as a yellow solid (566.00 mg, yield 83%).

Compound 8 (200.00 mg, 610.83 μmol) was dissolved in DCM (1 mL), and TFA (1 mL) was added. The reaction was stirred at room temperature for 3 h. After the completion of the reaction, TFA was removed by a rotary evaporator. A saturated $NaHCO_3$ solution (10 mL) was added. The aqueous phase was extracted with ethyl acetate. The combined organic phase was washed with a saturated brine solution (10 mL×1), dried over $Na_2SO_4$, and rotary evaporated to remove the solvent. The residue was purified by silica gel column chromatography to afford a yellow solid (130.00 mg, yield 93.6%).

Lipoic acid (50.00 mg, 242.34 μmol) was dissolved in DMF (3 mL). EDCI (139.37 mg, 727.01 μmol), HOBt (39.29 mg, 290.80 μmol), and triethylamine (100.78 μL, 727.01 μmol) were added and stirred at room temperature for 10 min. Then the yellow solid obtained from the above reaction (71.61 mg, 315.04 μmol) was added in one portion. The reaction was stirred at room temperature with argon-shield for 6 h. A saturated $NaHCO_3$ solution (10 mL) was added and the aqueous phase was extracted with ethyl acetate. The combined organic phase was washed with a saturated brine solution (10 mL×1), dried over $Na_2SO_4$ and rotary evaporated to remove the solvent. The residue was purified by silica gel column chromatography to afford a pale brown oil (53 mg, yield 52.6%). $^1$H NMR (400 MHz, DMSO) δ 9.12 (s, 1H), 8.40 (s, 1H), 8.14-8.02 (m, 1H), 7.46 (d, J=4.7 Hz, 1H), 7.28 (t, J=7.0 Hz, 1H), 6.93-6.80 (m, 1H), 6.12-5.98 (m, 1H), 4.63 (d, J=12.4 Hz, 1H), 4.03 (d, J=11.9 Hz, 1H), 3.85 (d, J=12.0 Hz, 1H), 3.62 (s, 2H), 3.51 (s, 1H), 3.24-2.99 (m, 4H), 2.91 (s, 1H), 2.43-2.30 (m, 2H), 2.15 (dd, J=38.2, 16.6 Hz, 3H), 1.93-1.65 (m, 5H), 1.63-1.33 (m, 7H), 1.22 (s, 1H). Purity: 99% (HPLC).

Example 5

Preparation of 1-(5-(1, 2-dithiolan-3-yl) pentanoyl)-N-(isoquinolin-5-yl) piperidine-4-carboxamide (PT106)

The Synthetic Scheme:

According to the above synthetic scheme of PT106, compound 9 (1 g, 7.74 mmol) was dissolved in NaOH solution (2 M, 10 mL). A solution of BOC anhydride (2.53 g, 11.61 mmol) in THF (10 mL) was slowly added in an ice bath. The reaction was stirred at room temperature for 1 h. THF was removed by a rotary evaporator. The aqueous phase was adjusted to pH 5-6 with diluted hydrochloric acid, and then extracted with ethyl acetate. The combined organic phases were dried over anhydrous $Na_2SO_4$ and filtered. The filtrate was concentrated by a rotary evaporator, and vacuum dried to give compound 10 as a white solid (1.78 g, 7.76 mmol, yield 100%).

Compound 10 (279.89 mg, 1.22 mmol), isoquinolin-5-amine (160.00 mg, 1.11 mmol) and DMAP (13.56 mg, 110.98 μmol) were dissolved in anhydrous DCM (8 mL). Triethylamine (461.50 μL, 3.33 mmol) and EDCI (319.12 mg, 1.66 mmol) were added at normal temperature, and stirred overnight at room temperature. After the completion of the reaction, it was quenched with water (10 mL). The aqueous phase was extracted with DCM. The combined organic phase was washed with a saturated brine solution (10 mL×1), dried over anhydrous $Na_2SO_4$, and rotary evaporated to remove the solvent. The residue was purified by silica gel column chromatography to give an intermediate 11 as a white solid (174.30 mg, 490.39 μmol, yield 44.2%). $^1$H NMR (400 MHz, $CDCl_3$) δ 9.27 (s, 1H), 8.57 (d, J=6.0 Hz, 1H), 8.16 (d, J=7.2 Hz, 1H), 7.84 (d, J=8.2 Hz, 1H), 7.64-7.57 (m, 3H), 4.37-4.10 (m, 2H), 2.86 (s, 2H), 2.59 (s, 1H), 2.05-2.01 (m, 2H), 1.89-1.79 (m, 2H), 1.48 (s, 9H).

The intermediate 11 (85.00 mg, 239.15 μmol) was dissolved in DCM (1 mL). TFA (1 mL) was added and stirred at room temperature for 3 h. After the completion of the reaction, TFA was removed by a rotary evaporator. Lipoic acid (59.21 mg, 286.98 μmol), DMAP (2.92 mg, 23.91 μmol) and EDCI (91.69 mg, 478.29 μmol) were added to the residue. Triethylamine (99.45 μL, 717.44 μmol) in anhydrous DCM was stirred overnight at room temperature. After the completion of the reaction, it was quenched with water (10 mL). The aqueous phase was extracted with DCM. The combined organic phase was washed with a saturated brine solution (10 mL×1), dried over anhydrous $Na_2SO_4$, and rotary evaporated to remove the solvent. The residue was purified by silica gel column chromatography to afford a yellow oil PT106 (77 mg, 173.57 μmol, yield 72.6%). $^1$H NMR (400 MHz, CDCl3) δ 9.22 (s, 1H), 8.51 (d, J=5.9 Hz, 1H), 8.12 (s, 1H), 8.06 (d, J=7.4 Hz, 1H), 7.81 (d, J=8.1 Hz, 1H), 7.60-7.56 (m, 2H), 4.65 (d, J=12.8 Hz, 1H), 3.96 (d, J=13.3 Hz, 1H), 3.59-3.52 (m, 1H), 3.23-3.05 (m, 3H), 2.76-2.67 (m, 11.2 Hz, 2H), 2.48-2.40 (m, 1H), 2.38-2.27 (m, 2H), 2.05 (d, J=12.5 Hz, 2H), 1.96-1.84 (m, 5H), 1.84-1.74 (m, 2H), 1.70-1.59 (m, 4H), 1.52-1.40 (m, 2H). $^{13}$C NMR (100 MHz, CDCl3) δ 173.34, 171.40, 153.09, 143.20, 131.67, 130.16, 129.12, 127.39, 125.49, 114.33, 56.55, 45.09, 43.75, 41.20, 40.37, 38.62, 34.82, 33.22, 29.19, 25.15. Purity: 96% (HPLC).

Example 6

Preparation of 4-(5-(1, 2-dithiolan-3-yl) pentanamido)-N-(isoquinolin-5-yl) benzamide (PT133)

The Synthetic Scheme:

-continued

PT133

According to the above synthetic scheme of PT133, compound 12 (200.00 mg, 1.39 mmol), isoquinolin-5-amine (427.86 mg, 1.80 mmol), DMAP (16.95 mg, 138.72 μmol) and triethylamine (576.87 μL, 4.16 mmol) were dissolved in anhydrous DCM. The reaction was stirred at room temperature for 30 min. and then EDCI (797.80 mg, 4.16 mmol) was added in one portion. The reaction was refluxed overnight. After the completion of the reaction, it was quenched with water (10 mL). The aqueous phase was extracted with DCM. The combined organic phase was washed with saturated brine solution (10 mL×1), dried over anhydrous Na$_2$SO$_4$, and rotary evaporated to remove the solvent. The residue was purified by silica gel column chromatography to give an intermediate 13 as a white solid (426, 1.17 mmol, yield 84.5%). $^1$H NMR (400 MHz, DMSO) δ 10.36 (s, 1H), 9.71 (s, 1H), 9.35 (s, 1H), 8.52 (d, J=5.9 Hz, 1H), 8.03 (t, J=8.3 Hz, 3H), 7.88 (d, J=7.3 Hz, 1H), 7.82 (d, J=5.6 Hz, 1H), 7.72 (t, J=7.7 Hz, 1H), 7.63 (d, J=8.1 Hz, 2H), 1.51 (s, 9H).

The intermediate 13 (80.00 mg, 220.14 μmol) was dissolved in DCM (1 mL). Then TFA (1 mL) was added and stirred at room temperature for 3 h. After the completion of the reaction, TFA was removed by a rotary evaporator. Lipoic acid (54.50 mg, 264.16 μmol), DMAP (2.69 mg, 22.01 μmol) and EDCI (126.60 mg, 660.41 μmol) were added to the residue. Then triethylamine (91.54 μL, 660.41 μmol) in anhydrous DCM (6 mL) was added and stirred overnight at room temperature. After the completion of the reaction, it was quenched with water (10 mL). The aqueous phase was extracted with DCM. The combined organic phase was washed with a saturated brine solution (10 mL×1), dried over anhydrous Na$_2$SO$_4$, and rotary evaporated to remove the solvent. The residue was purified by silica gel column chromatography to afford a white solid PT133 (54.40 mg, 120.46 μmol, yield 54.7%). m.p. 172.6° C. $^1$H NMR (400 MHz, DMSO) δ 10.41 (s, 1H), 10.20 (s, 1H), 9.38 (s, 1H), 8.53 (d, J=6.0 Hz, 1H), 8.08-8.03 (m, 3H), 7.91 (d, J=7.3 Hz, 1H), 7.85 (d, J=6.0 Hz, 1H), 7.78 (s, 1H), 7.76 (d, J=2.3 Hz, 1H), 7.73 (d, J=7.8 Hz, 1H), 3.69-3.60 (m, 1H), 3.21-3.13 (m, 3H), 2.46-2.35 (m, 3H), 1.83-1.93 (m, 1H), 1.78-1.55 (m, 4H), 1.47-1.42 (m, 2H). $^{13}$C NMR (100 MHz, DMSO) δ 172.11, 166.12, 152.97, 143.15, 142.98, 133.77, 131.84, 129.33, 128.73, 127.80, 127.66, 126.00, 118.72, 116.89, 113.08, 56.59, 38.60, 36.80, 34.64, 28.82, 25.24. Purity: 97% (HPLC).

Example 7

Preparation of 4-(5-(1, pentanamido)-N-(pyridin-4-yl)benzamide (PT119)

The Synthetic Scheme:

PT119

According to the above synthetic scheme of PT119, compound 14 (1.00 g, 5.15 mmol) was dissolved in DCM (2 mL). And TFA (2 mL) was added and stirred at room temperature for 3 h. After the completion of the reaction, TFA was removed by a rotary evaporator to afford a crude product 4-aminopyridine trifluoroacetate.

4-aminopyridine trifluoroacetate (300.00 mg, 1.45 mmol), N-BOC-4-aminobenzoic acid (377.99 mg, 1.59 mmol) and DMAP (17.69 mg, 144.84 μmol) were dissolved in the in anhydrous DCM (6 mL). Triethylamine (602.30 μL, 4.35 mmol) and EDCI (416.48 mg, 2.17 mmol) were added at room temperature. The reaction was stirred at room temperature overnight. After the completion of the reaction, it was quenched with water (10 mL). The aqueous phase was extracted with DCM. The combined organic phase was washed with a saturated brine solution (10 mL×1), dried over anhydrous Na$_2$SO$_4$, and rotary evaporated to remove the solvent. The residue was purified by silica gel column chromatography to give an intermediate 15 as a white solid (140 mg, 446.78 yield 54.7%). $^1$H NMR (400 MHz, DMSO) δ 10.41 (s, 1H), 9.72 (s, 1H), 8.45 (d, J=4.6 Hz, 2H), 7.90 (d, J=8.3 Hz, 2H), 7.77 (d, J=4.9 Hz, 2H), 7.60 (d, J=8.3 Hz, 2H), 1.49 (s, 9H).

The intermediate 15 (50.00 mg, 159.57 μmol) was dissolved in DCM (1 mL). And TFA was added and stirred at room temperature for 3 h. After the completion of the reaction, TFA was removed by a rotary evaporator. Lipoic acid (32.92 mg, 159.57 μmol), HOBt (25.87 mg, 191.48 μmol) and EDCI (45.88 mg, 239.35 μmol) were added to the residue. A solution of triethylamine (66.36 μL, 478.70 μmol) in anhydrous DCM (4 mL) was added and stirred at room temperature overnight. After the completion of the reaction, it was quenched with water (10 mL). The aqueous phase was extracted with DCM. The combined organic phase was washed with a saturated brine solution (10 mL×1), dried over anhydrous $Na_2SO_4$, and rotary evaporated to remove the solvent. The residue was purified by silica gel column chromatography to afford a white solid PT119 (48 mg, 119.54 μmol, yield 74.91%). m.p. 159.9° C. $^1$H NMR (400 MHz, DMSO) δ 10.44 (s, 1H), 10.21 (s, 1H), 8.45 (s, 2H), 7.94 (d, J=7.4 Hz, 2H), 7.75 (d, J=9.1 Hz, 4H), 3.63 (s, 1H), 3.15 (d, J=20.1 Hz, 2H), 2.36 (s, 3H), 1.90-1.86 (m, 1H), 1.61 (s, 4H), 1.42 (s, 2H). 13C NMR (100 MHz, DMSO) δ 171.64, 165.72, 150.19, 146.05, 142.75, 128.86, 128.11, 118.20, 113.94, 56.07, 38.08, 36.27, 34.11, 28.27, 24.69. Purity: 97% (HPLC).

Example 8

Preparation of 1-(5-(1, 2-dithiolan-3-yl) pentanoyl)-N-(pyridin-4-yl) piperidine-4-carboxamide (PT134)

The Synthetic Scheme:

According to the above synthetic scheme of PT134, 4-aminopyridine trifluoroacetate (200.00 mg, 965.58 μmol) obtained from example 7, compound 10 (265.66 mg, 1.16 mmol), and DMAP (11.80 mg, 96.56 μmol) were dissolved in anhydrous DCM (6 mL). Triethylamine (401.53 μL, 2.90 mmol) and EDCI (555.31 mg, 2.90 mmol) were added and stirred overnight at room temperature. After the completion of the reaction, it was quenched with water (10 mL). The aqueous phase was extracted with DCM. The combined organic phase was washed with a saturated brine solution (10 mL×1), dried over anhydrous $Na_2SO_4$, and rotary evaporated to remove the solvent. The residue was purified by silica gel column chromatography to give an intermediate 16 as a white solid (281 mg, 920.19 μmol, yield 95.3%). $^1$H NMR (400 MHz, DMSO) δ 10.29 (s, 1H), 8.40 (d, J=4.8 Hz, 2H), 7.56 (d, J=4.8 Hz, 2H), 3.99 (d, J=14.2 Hz, 3H), 2.86-2.67 (m, 2H), 1.79 (d, J=12.9 Hz, 2H), 1.51-1.45 (m, 2H), 1.40 (s, 9H). Compound 16 (140.00 mg, 458.46 μmol) was dissolved in DCM (1 mL). TFA (1 mL) was added and stirred at room temperature for 3 h. After the completion of the reaction, TFA was removed by a rotary evaporator. Lipoic acid (113.51 mg, 550.15 μmol), DMAP (5.60 mg, 45.85 μmol), EDCI (263.66 mg, 1.38 mmol) and DMF (1 mL) were added to the residue. Finally, triethylamine (190.65 μL, 1.38 mmol) in anhydrous DCM (6 mL) was added and stirred overnight at room temperature. After the completion of the reaction, it was quenched with water (10 mL). The aqueous phase was extracted with DCM. The combined organic phase was washed with a saturated brine solution (10 mL×1), dried over anhydrous $Na_2SO_4$, and rotary evaporated to remove the solvent. The residue was purified by silica gel column chromatography to afford a pale brown oil PT134 (154.3 mg, 392.06 μmol, yield 85.52%). $^1$H NMR (400 MHz, $CDCl_3$) δ 8.47 (d, J=5.3 Hz, 2H), 8.34 (s, 1H), 7.51 (d, J=5.4 Hz, 2H), 4.59 (d, J=13.4 Hz, 1H), 3.94 (d, J=13.5 Hz, 1H), 3.66-3.48 (m, 1H), 3.25-3.01 (m, 3H), 2.68 (t, J=12.2 Hz, 1H), 2.59-2.41 (m, 2H), 2.35 (t, J=7.4 Hz, 2H), 1.94-1.91 (m, 2H), 1.81-1.79 (m, 1H), 1.72-1.63 (m, 6H), 1.52-1.45 (m, 3H). $^{13}$C NMR (100 MHz, $CDCl_3$) δ 173.78, 171.51, 150.35, 145.93, 113.98, 56.53, 45.02, 43.83, 41.17, 40.37, 38.61, 34.79, 33.21, 29.14, 25.19. Purity: 98% (HPLC).

Example 9: Biological Evaluation

The Protective Effect of Compounds on Glutamate-induced HT22 Cells death

Figure 1:
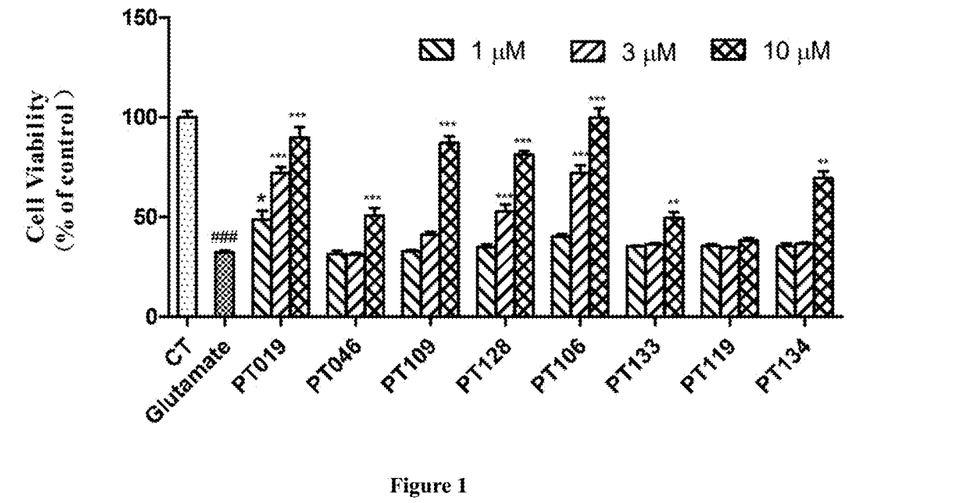
FIG. 1. The protective effect of compounds on glutamate-induced HT22 cells death. *P<0.001, P<0.01, **P<0.05 vs. glutamate treated group; ### P<0.001 vs. control group.
Figure 2:
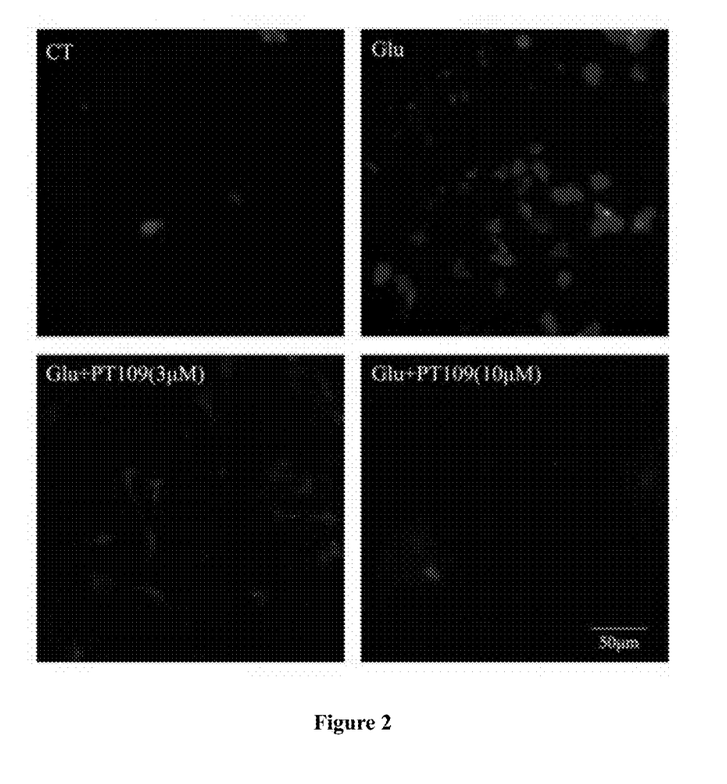
FIG. 2. The Effect of the compound PT109 on ROS.

Logarithmic phase of HT-22 cells were digested with 0.25% trypsin, resuspended in complete medium, and counted with a cell counting chamber under a microscope. The cell density was adjusted to 10×10$^4$ cells/mL. Then the cells were seeded in a 96-well plate at 100 μL/well, and cultured overnight to allow the cells to adhere. The medium in the 96-well plate was aspirated and compounds in various concentration were added to the 96-well plate at 100 μL/well. 2 μL of 100 mM L-glutamate was added after the preincubation for 30 min. The model group was not added with the test compound, and 2 μL of 100 mM L-glutamate was directly added. After incubation for 24 h, 10 μL of 5 mg/mL MTT was added to each well, and incubated for 1 h. The supernatant was discarded, and DMSO at 100 μL/well was added. The product formazan was vibrated to make it fully dissolved, and the absorbance of each well was measured at the wavelength 570 nm on the microplate reader. Cell viability was calculated by the formula compound-promoting cell survival rate (%)=100%*(A test compound−A model group)/(A model group−A control). The results are shown in FIG. 1. It can be seen from the results that the other compounds could reverse glutamate-induced HT-22 cells death at a certain concentration, except for the compound PT119.

Example 10: Biological Evaluation

The effect of PT109 on ROS
DHE staining was adopted to detect the formation of oxygen free radicals. The HT-22 cells were cultured in DMEM+10% fetal bovine serum and placed in a 5% $CO_2$ incubator at 37° C. The cells were seeded in a poly-lysine-coated 24-well plate at a suitable density. After cell adherence, the PT109 separately prepared in the medium was added to the corresponding wells. Upon treatment for 30 min, 2 mM glutamine was added and treated for 10 h. The cells were harvested, and incubated with DHE dye for about 30 min. DHE dye was washed, and the fluorescence intensity of DHE was detected by a high-content system. The experimental results show that glutamine-induced ROS elevation can be significantly reduced by PT109 at 10 μM.

Example 11: Biological Evaluation

The Inhibitory Effect of PT109 on SGK1 and JNK

The inhibitory effect of PT109 on SGK and JNK was detected by the kinase screening commercialization service of Life Technologies Corporation. As shown in Table 1, $IC_{50}$ of PT109 was 1.34 μM, 5.6 μM and 26.4 μM for SGK1, SGK2 and SGK3, respectively. PT109 has a better specificity for SGK1. Its $IC_{50}$ was 0.285 μM, 0.143 μM and 0.831 μM for JNK1, JNK2 and JNK3, respectively.

TABLE 1

The Inhibitory Effect of PT109 on SGK1 and JNK

| Kinase Tested | $IC_{50}$ (μM) |
|---|---|
| MAPK10 (JNK3) | 0.285 |
| MAPK8 (JNK1) | 0.143 |
| MAPK9 (JNK2) | 0.831 |
| SGK (SGK1) | 1.34 |
| SGK2 | 5.6 |
| SGK3 | 26.4 |

Example 12: Biological Evaluation

The Kinase Selectivity of PT109

The inhibitory effect of PT109 on other kinases including SGK and JNK was detected by the Kinase Screening Service of Life Technologies Corporation (The concentration of compound 9 was 10 μM, measurements were performed in duplicates, and the value was represented by an average) to investigate the selectivity of the compound for JNK and SGK1. As shown in Table 2, PT109 at 10 μM has a better specificity for SGK1 and JNK.

TABLE 2

The inhibitory effect of PT109 on other kinases

| Kinase Tested | % Inhibition | Kinase Tested | % Inhibition |
|---|---|---|---|
| ADRBK1 (GRK2) | 6 | PRKCA (PKC alpha) | 25 |
| AKT1 (PKB alpha) | 22 | PRKCB1 (PKC beta I) | −10 |
| AKT2 (PKB beta) | 30 | PRKCG (PKC gamma) | 63 |
| AURKC (Aurora C) | 5 | PRKCH (PKC eta) | −17 |
| CDK1/cyclin B | 14 | PRKCI (PKC iota) | −14 |
| CDK5/p25 | 18 | PTK2B (FAK2) | 8 |
| CDK5/p35 | 26 | PTK6 (Brk) | 7 |
| CSNK1A1 (CK1 alpha 1) | 3 | RPS6KA3 (RSK2) | 54 |
| CSNK1D (CK1 delta) | 6 | RPS6KA4 (MSK2) | 28 |
| CSNK1E (CK1 epsilon) | 10 | SGK (SGK1) | 91 |
| CSNK1G1 (CK1 gamma 1) | 9 | SRMS (Srm) | 20 |
| CSNK1G2 (CK1 gamma 2) | 15 | STK22D (TSSK1) | −2 |
| CSNK1G3 (CK1 gamma 3) | 24 | TAOK2 (TAO1) | −6 |
| CSNK2A1 (CK2 alpha 1) | 14 | TBK1 | 10 |
| CSNK2A2 (CK2 alpha 2) | 11 | TYRO3 (RSE) | 12 |
| DYRK1A | 16 | CHUK (IKK alpha) | 16 |
| EGFR (ErbB1) | −6 | PI4KB (PI4K beta) | 39 |
| FGFR1 | −3 | PIK3C2A (PI3K-C2 alpha) | 3 |
| FGFR4 | −2 | PIK3C3 (hVPS34) | 11 |
| FLT1 (VEGFR1) | 3 | PIK3CA/PIK3R1 (p110 alpha/p85 alpha) | 56 |
| GRK5 | 2 | PIK3CD/PIK3R1 (p110 delta/p85 alpha) | 48 |
| GSK3A (GSK3 alpha) | 41 | PIK3CG (p110 gamma) | 9 |
| GSK3B (GSK3 beta) | 61 | MAP2K1 (MEK1) S218D S222D | 13 |
| HCK | 9 | MAP3K2 (MEKK2) | 10 |
| HIPK1 (Myak) | 0 | MAP3K3 (MEKK3) | 3 |
| LTK (TYK1) | 40 | MAP3K5 (ASK1) | 9 |
| MAP3K9 (MLK1) | 2 | MAP3K7/MAP3K7IP1 (TAK1-TAB1) | 39 |
| MAP4K4 (HGK) | 34 | MAPK10 (JNK3) | 90 |
| MAPK1 (ERK2) | 4 | MAPK8 (JNK1) | 104 |
| MST1R (RON) | 35 | MAPK9 (JNK2) | 91 |
| NEK4 | 3 | MKNK2 (MNK2) | 26 |
| NEK6 | 3 | MYO3B (MYO3 beta) | 43 |
| NEK7 | 2 | PLK4 | 35 |
| NTRK1 (TRKA) | 35 | SLK | 5 |
| NTRK3 (TRKC) | 28 | TEC | 26 |
| PAK6 | −16 | TLK1 | 20 |
| PDGFRB (PDGFR beta) | 7 | ULK1 | 26 |
| PDK1 Direct | 51 | ULK2 | 4 |
| PDK1 | 5 | WNK2 | 13 |
| PHKG1 | 10 | WNK3 | 7 |
| PKN1 (PRK1) | 16 | | |

Example 13: Biological Evaluation

In Vitro Blood-brain Barrier Permeability 1) 4 μL of 2% PBL solution was added to the hydrophobic membrane of a MAIPn 4550 96-well plate. During the dripping process, it should be noted that the pipette tip should not touch the surface of the membrane to avoid the damage to the membrane structure.

2) 200 μL of the test sample solution (0.1 mg/ml) was quickly (within 10 min) and quantitatively pipetted, and added to the upside of the membrane of the 96-well plate as a donor compartment. 200 μL of PBS (pH=7.4) was added to the other side of the membrane as an acceptor compartment. It should be noted that the acceptor solution should keep being in full contact with the membrane.

3) The donor compartment was carefully removed upon standing for 120 min at room temperature, and the absorbance of the compound (250-500 nm) in the acceptor compartment was tested by UV spectrometer.

4) 100 μL of the test sample solution was fully mixed with 100 μL of PBS, and the mixture was used as a theoretical equilibrium solution. Its absorbance (250-500 nm) was measured and tested with an acceptor plate.

5) The log $P_e$ value was calculated by the following equation:

$$P_e = -\left(\frac{V_d \times V_a}{(V_d + V_a)A \times t}\right) \times \ln\left(1 - \frac{[\text{drug}]_{acceptor}}{[\text{drug}]_{equilibrium}}\right)$$

wherein $V_d$ is the volume of the donor compartment, $V_a$ is the volume of the acceptor compartment, A is the membrane area, t is the penetration time, $[\text{drug}]_{acceptor}$ is the absorbance of the acceptor compartment, and $[\text{drug}]_{equilibrium}$ is the absorbance of theoretical equilibrium.

Note: If $P_e \times 10^{-6}$ cm s$^{-1}$ value is greater than 5.3, the compound is able to cross the blood-brain barrier. If the value less than 2.4, the compound is defined as inability to penetrate the blood-brain barrier. As shown in the result table 3, PT109 has a better blood-brain barrier permeability.

TABLE 3

Blood-brain barrier permeability of PT109

| Compound | $P_e$ (×10$^{-6}$ cm s$^{-1}$) | Prediction | M.W | cLogP |
|---|---|---|---|---|
| PT109 | 11.93 ± 0.08 | CNS+ | 429.19 | 4.26 |

What is claimed is:

1. A compound of following structural formula:

Formula (I)

or a pharmaceutically acceptable salt thereof, wherein X is selected from:

-continued

Y is selected from:

Z is selected from:

2. The pharmaceutical composition comprising any of the compounds or the pharmaceutically acceptable salts thereof of claim 1, and a pharmaceutically acceptable carrier or excipient.

* * * * *